United States Patent
Rau et al.

[11] Patent Number: 6,116,862
[45] Date of Patent: Sep. 12, 2000

[54] BLOOD PUMP

[75] Inventors: Guenter Rau, Aachen; Helmut Reul, Dueren; Thorsten Siess, Aachen, all of Germany

[73] Assignee: MEDOS Medizintechnik GmbH, Stolberg, Germany

[21] Appl. No.: 09/202,538
[22] PCT Filed: Jun. 4, 1997
[86] PCT No.: PCT/EP97/02904
  § 371 Date: Dec. 16, 1998
  § 102(e) Date: Dec. 16, 1998
[87] PCT Pub. No.: WO97/49439
  PCT Pub. Date: Dec. 31, 1997

[30] Foreign Application Priority Data

Jun. 25, 1996 [DE] Germany .................. 196 25 300

[51] Int. Cl.$^7$ ...................................... F04B 9/00
[52] U.S. Cl. .................. 417/319; 417/366; 417/420; 417/423.1; 417/423.12; 604/151
[58] Field of Search .................. 417/319, 366, 417/420, 423.1, 423.12, 423.13, 423.14; 604/151

[56] References Cited

U.S. PATENT DOCUMENTS

| | | |
|---|---|---|
| 4,135,253 | 1/1979 | Reich et al. ........................ 3/1.7 |
| 4,994,078 | 2/1991 | Jarvik ............................. 623/3 |
| 5,147,186 | 9/1992 | Buckholtz ....................... 417/420 |
| 5,324,177 | 6/1994 | Golding et al. ................ 417/423.1 |
| 5,393,207 | 2/1995 | Maher et al. .................. 417/423.7 |
| 5,692,882 | 12/1997 | Bozeman, Jr. et al. ............ 417/45 |
| 5,695,471 | 12/1997 | Wampler ......................... 604/131 |
| 5,840,070 | 11/1998 | Wampler ......................... 604/131 |
| 5,890,883 | 4/1999 | Allen et al. ..................... 404/112 |
| 6,015,272 | 1/2000 | Antaki et al. ................... 417/356 |
| 6,042,347 | 3/2000 | Scholl et al. ................. 417/423.12 |

*Primary Examiner*—Teresa Walberg
*Assistant Examiner*—Jeffrey Pwu
*Attorney, Agent, or Firm*—Diller, Ramik & Wight, PC

[57] ABSTRACT

The blood pump (BP) has an elongate tubular pump housing (10) wherein a motor (16) is arranged that drives a pump impeller wheel (22), the pump housing having an inlet (12) at one end and an outlet (18) at the opposite end. The motor (16) comprises a motor housing (15) sealed off against the blood flow. The pump impeller wheel (22) is located at the end of the motor housing (15) facing the inlet (12) and, together with a transition portion (13) of the pump housing (10), forms a rotary pump flown through diagonally, which creates an axial flow flowing around the motor housing (15). Here, the blood flow exclusively flows between stationary parts, thereby reducing the risk of blood decay caused by shear stresses.

16 Claims, 3 Drawing Sheets

BLOOD PUMP

BACKGROUND OF THE INVENTION

The present invention refers to a blood pump, preferably to an implantable blood pump for supporting or replacing the cardiac function on the left and/or the right hand side.

From U.S. Pat. No. 4,994,078, an implantable blood pump is known that is shaped like a snail shell, the stator of the motor being integrated in the pump housing, while the rotor is firmly connected to a pump impeller wheel and is flushed by the blood flow. Thus, the blood flows through the inside of the motor, with one wall of the annular channel formed by the motor being stationary, while the other wall rotates. This gives rise to the risk of damage to the blood caused by shear forces occurring there.

EP 0 611 580 A2 describes an artificial cardiac pump, wherein blood also flows around the rotor and the stator of the motor. At the outlet side, a pump impeller wheel is arranged that is designed as a radial pump and pumps blood, drawn axially along the stator, into a surrounding annular channel from which the blood exits tangentially. Here, there are two suction paths, namely the main suction path surrounding the stator and a relatively narrow annular channel between the stator and the rotor. Again, there is a risk of damaging the blood by shear forces.

Finally, a blood pump is known from WO 94/09274 that has a helical rotor surrounding a stator.

It is the object of the present invention to provide a blood pump in which damage to the blood and thrombogenesis are substantially avoided.

According to the invention, the object is solved with the features of claim 1.

SUMMARY OF THE INVENTION

In the blood pump of the present invention, the motor is disposed coaxially as a self-contained unit inside an elongate pump housing, an annular channel being formed between the pump housing and the motor housing, through which channel blood flows. The pump impeller wheel is arranged at the inlet end of the motor and, together with a transition portion of the pump housing, forms a pump that is flown through diagonally and creates an whirling axial flow flowing annularly around the motor housing. Thus, in the region of the motor, the blood flows between two stationary parts, namely the pump housing and the motor housing, whereby additional shearing stresses of the blood outside the rotating part of the pump blades are avoided. The blood flow passing along the motor housing causes a constant cooling of the motor for as long as the motor operates. Accordingly, the motor is cooled by the blood flowing along the same. The pump housing is elongate and substantially tubular and formed without any rotating annular channels or other enlargements. This allows for a simple and compact implantation in the vicinity of the heart, taking into consideration the physiological boundary conditions.

The axial blood flow along the pump housing may have a circumferential component, the blood flowing helically around the motor housing. The pump housing has a length of about 5 to 10 cm and an outer diameter of about 2 to 3 cm. The inlet and the outlet are tapered with respect to the outer diameter of the pump housing.

In a preferred embodiment of the blood pump, the outlet exits on the side of the pump housing. Here, an end wall may be provided at the outlet end of the pump housing, the wall including a helical channel leading to the outlet at the angle of the flow present there. Such a blood pump is particularly suited for patients having irreversible cardiac failure of the left ventricle. In this case, a connection site is inserted into the ventricle so that the same is relieved by taking blood therefrom. The connection site is connected to the pump inlet, while the outlet of the pump is connected to the aorta. The outlet of this embodiment, shifted by about 90° with respect to the inlet, is physiologically favorable also for a cannulation between left atrium and aorta.

The connection of the inlet of the blood pump with the atrium may be closed again after removal of the connection site. Thus, the heart may return to working on its own again. This method is preferred, if there is a chance for a long-term recovery of the heart or when the pump is intended to serve as a chronic supporting pump for the still active, though in a reduced degree, heart.

In another embodiment of the blood pump, the outlet exits axially from the pump housing.

The following is a detailed description of embodiments of the invention with reference to the drawings.

In the Figures:

DESCRIPTION OF THE PREFERRED EMBODIMENTS

Figure 1:
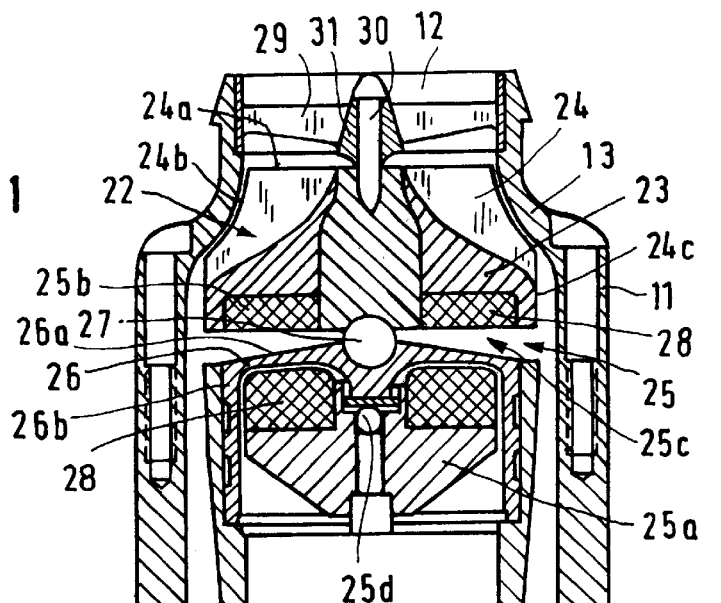
FIG. 1 is a longitudinal section through a first embodiment of the blood pump.

The blood pump BP of FIG. 1 has an elongate tubular pump housing 10 having one end provided with an inlet member 11. The inlet member 11 has an inlet 12, the inner diameter of which is smaller than the inner diameter of the pump housing 10. The inlet member 11 is formed with an annular transition portion 13 of arcuate shape and passing smoothly and without kinks in a S-shape from the diameter of the inlet 12 to the inner diameter of the pump housing 10.

At the end of the pump housing 10 opposite the inlet 12, an end wall 14 is provided for closing off the pump housing. Fixed to this end wall 14 is the motor housing 15 of a motor 16, the motor being an electric motor. The motor housing 15 protrudes from the end wall 14. It is sealed off completely, the electric wires being passed through a passage 17 into the motor housing 15.

The outlet 18 is disposed at a tubular outlet piece 19 tangentially extending from the end wall 14 in a lateral direction. Within the end wall 14, a helical channel 20 extends exclusively axially in the direction of the whirling axial flow from 21 to the outlet 18.

Arranged in the inlet portion 11 of the pump housing 10, there is a pump impeller wheel 22. This comprises a hub 23 from which blades 24 project. The pump impeller wheel 22 is driven by the motor 16 via a magnetic clutch that may be a rotary end clutch 25 or a rotary central clutch. The clutch comprises a first clutch member 25a connected with the rotor of the motor 16 and encapsulated within the motor housing 15, and a second clutch member 25b provided in the hub 23 of the pump impeller wheel 22. Both coupling members 25a, 25b comprise magnets 28 causing the second clutch member 25b to rotate along with the first clutch member 25a should the same be rotated.

The motor housing 15 is closed with a non-magnetic non-conductive cap 26 on which a combined axil/radial bearing 27 in the form of a sphere is supported. This bearing in turn supports the hub of the pump impeller wheel 22. The magnets 28 of the rotary end clutch 25 generate an axial retaining force that is greater than the reaction force created when rotating the pump impeller wheel 22 so that the pump impeller wheel 22 is pulled towards the motor 16 and pressed against the bearing 27 by magnetic force. The axial retaining force of the clutch 25 is centrally compensated on the cap 26 by a further axial bearing support 25d in combination with the bearing 27 so that neither the bearings of the motor 26, nor the thin cap 26 have to absorb this force in their circumferential wall 26b and on the front end face 26a.

To center the pump impeller wheel 22 on the inlet side, a spider 29 is mounted in the inlet 12 having a journal 30 that engages axially into the hub 23 of the pump impeller wheel 22. The spider 29 is provided with a centered head member 31 surrounding the journal 30 and deflecting the incoming axial flow slightly radially towards the hub 23.

The guide blades 24 of the pump impeller wheel 22 have an outer diameter at the inflow end 24a that substantially corresponds to the diameter of the inlet 12 so that, at this location, the pump impeller wheel covers the entire diameter of the inlet channel. The inlet edges 24a pass into a concave arcuate circumferential portion 24b that follows the transition portion 13 of the pump housing with a small clearance. Contiguous thereto, the pump blades 24 comprise a portion 24c with a diameter about as large as the outer diameter of the motor housing 15 at the end facing the pump impeller wheel 22. The outer diameter of the diagonal pump blades 24 is made as large as made possible by the overall diameter of the transition portion 13. Thus, the required hydraulic power can be obtained at a comparatively low number of rotations (for example, n≡7000 U/min for V/t≡51/min and ΔP≡100 mmHg), whereby the life time of the bearing components of the pump is increased.

Between the pump housing 10 and the motor housing 15, there is an annular channel 35 that extends in the longitudinal direction. This annular channel 35 is designed as a diffusor by increasing its cross sectional area from the inlet to the outlet. This causes a slow-down of the blood flow and, thereby, a pressure increase. The enlargement of the sectional area of the annular channel 35 is obtained by corresponding changes in the wall thickness of the pump housing 10 and the motor housing 15.

The motor 16 causes the pump impeller wheel 22 to rotate, the blades 24 of the pump impeller wheel being helical in shape. Thereby, blood is drawn axially from the inlet 12 and conveyed into the annular channel 25 with a rotary circumferential component. From there, the blood passes through the helical channel 20 to the lateral outlet 18, the course and pitch of the channel being adapted to that of the rotating blood flow.

Figure 2A:
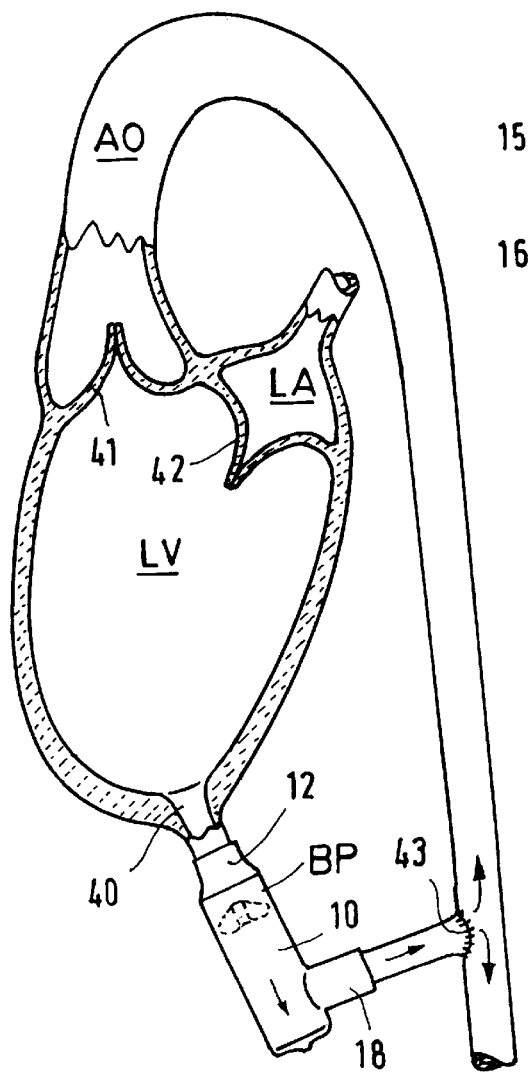
FIGS. 2a and 2b are schematic illustrations of the implementation of the blood pump at the heart.

FIG. 2a illustrates the blood pump BP of FIG. 1 in the state in which it is implanted near the heart. A hose connects the inlet 12 of the blood pump BP to a port 40 made in the left ventricle LV. In the Figure, the aorta AO, the aortic valve 41, the left atrium LA and the mitral valve 42 are discernible. The outlet 18 of the blood pump BP is connected with a port 43 to the aorta AO.

Figure 2B:
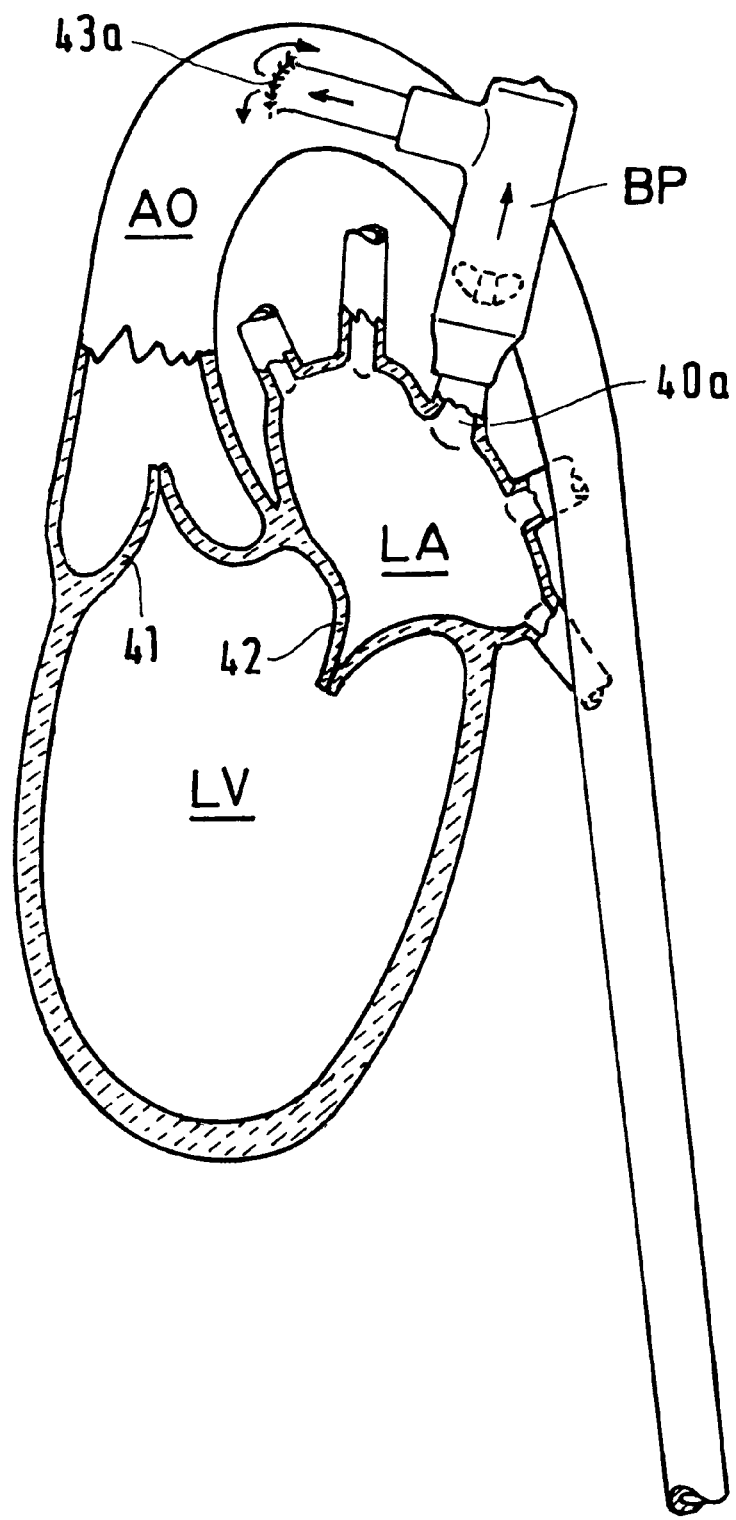

Alternatively, the blood pump BP of FIG. 2b may be connected to a port 40a made in the left atrium LA and convey blood into the aorta AO via a port 43a.

From FIG. 2, it is evident that the lateral extension of the outlet 18 from the pump housing 10 facilitates the arrangement of the blood pump near the heart and its connection to the heart/vestibule, on the one hand, and to the aorta, on the other hand.

Figure 3:
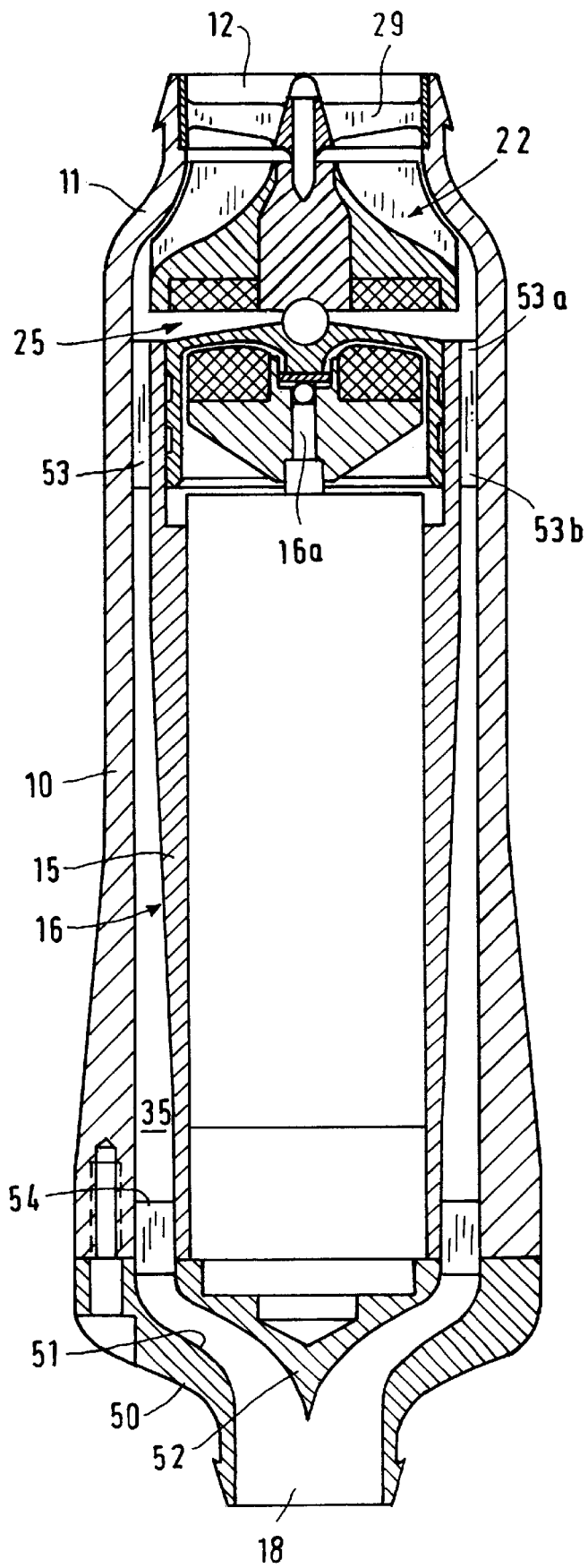
FIG. 3 is a second embodiment of the blood pump with the inlet and the outlet directed axially.

In the blood pump shown in FIG. 3, the outlet 18 is arranged coaxial to the inlet 12. It is part of an outlet member 50 formed similar to the inlet member 12 and having an arcuate transition portion 51 leading from the annular channel 35 to the outlet 18 in a manner favorable for the flow. For the same purpose, the rear end of the motor housing 15 is provided with a projection 52 tapering continuously in the direction of the flow.

To keep the motor housing 15 centered in the pump housing 10, radial guide blades 53, 54 are provided that serve, on the one hand, to hold the motor housing and, on the other hand, to guide the rotary blood flow. In the portion 53a, the guide blades 53 have a relatively large angle of attack (with respect to the axial direction) which is selected such that the guide blades are flown against without any flow separation. In the rear portion 5b, the angle of attack is smaller. Thus, a great part of the rotation energy is withdrawn from the blood coming from the pump impeller wheel 22 and is purposefully converted into pressure. The guide blades 54 have a smaller angle of attack. The angles of attack substantially correspond to the rotation of the flow at the respective locations.

Otherwise, the blood pump of FIG. 3 is constructed the same as the blood pump of FIG. 1. It is provided with a magnetic coupling 25 for driving the pump impeller wheel 22. As an alternative, the pump impeller wheel 22 may be connected directly with the motor shaft 16a, requiring, however, a shaft seal at the motor housing.

Although a preferred embodiment of the invention has been specifically illustrated and described herein, it is to be understood that minor variations may be made in the apparatus without departing from the spirit and scope of the invention, as defined the appended claims.

What is claimed is:

1. A blood pump for supporting or replacing the cardiac function, comprising a pump housing (10) in which a motor (16) is arranged that drives a pump impeller wheel (22), and which has an inlet (12) at one end and an outlet (18) at the other end, the motor (16) comprising a motor housing (15) concentrically arranged in the pump housing (10) and sealed off against the blood flow, the pump impeller wheel (22) being arranged at the end of the motor housing (15) that faces the inlet (12) and forming a rotary pump with a transition portion (13) of the pump housing (10), which pump creates an axial flow annularly flowing about the motor housing (15), and said axial flow being enclosed by stationary walls, characterized in that the pump housing is elongate and tubular and that an annular channel (35) directing a whirling helical flow is provided between the pump housing (10) and the motor housing (15).

2. The blood pump of claim 1, characterized in that the outlet (18) exits axially from the pump housing (10).

3. The blood pump of claim 1, characterized in that the outlet (18) exits tangentially from the side of the pump housing (10).

4. The blood pump of claim 3, characterized in that an end wall (14) is provided at the outlet end of the pump housing (10), the wall comprising a helical channel (20) leading to the outlet (18).

5. The blood pump of one of claim 1, characterized in that the motor housing (15) is fastened to the end wall (14) in a cantilevered manner.

6. The blood pump of claim 4, characterized in that the helical channel (20) leading to the outlet (18) passes into the outlet (18) without increasing the diameter of the pump housing (10).

7. The blood pump of one of claim 4, characterized in that the axial pitch of the helical channel (20) corresponds to that of the whirling flow so that the fluid is passed into the outlet (18) without any impact.

8. The blood pump of claim 1, characterized in that the annular channel (35) is formed as a diffusor, the sectional area of which increases towards the outlet (18).

9. The blood pump of claim 1, characterized in that guide blades (53, 54) are arranged in the annular channel (35) between the pump housing (10) and the motor housing (15), the blades holding the motor housing (10) and having a helical inclination.

10. The blood pump claim 1, characterized in that the largest diameter of the pump impeller wheel (22) is at least almost equal the largest outer diameter of the motor housing (15).

11. The blood pump of claim 1, characterized in that the pump housing (10) has a substantially cylindrical outer shape over its entire length, the inlet (12) and/or the outlet (18) possibly being tapered.

12. The blood pump of claim 1, characterized in that the moment of the motor (16) is transmitted to the pump impeller wheel (22) via a magnetic clutch (25).

13. The blood pump of claim 1, characterized in that te moment is transferred directly from the motor (16) to the pump impeller wheel (22) via a continuous shaft with a seal.

14. The blood pump of claim 13, characterized in that the pump impeller wheel is mechanically centered (27, 63) in the blood.

15. The blood pump of claim 12, characterized in that the pump impeller wheel (22) is centered in that blood by a combination of magnetic and mechanic bearing (27).

16. The blood pump of claim 12, characterized in that the axial force of the clutch is compensated directly on the center of a cap (26), whereby this component and the bearings of the motor (16) are subjected to substantially less axial loading.

* * * * *